(12) United States Patent
Lee et al.

(10) Patent No.: US 6,764,449 B2
(45) Date of Patent: Jul. 20, 2004

(54) METHOD AND APPARATUS FOR ENABLING A BIOPSY NEEDLE TO BE OBSERVED

(75) Inventors: Ki-Jong Lee, Yongin-si (KR); Moo-Ho Bae, Seoul (KR); Sang-Bum Gye, Seoul (KR); Jae-Sub Hwang, Seoul (KR); Young-Seuk Song, Seoul (KR); Gi-Duck Kim, Incheon (KR)

(73) Assignee: Medison Co., Ltd., Hongchun-gun (KR)

( * ) Notice: Subject to any disclaimer, the term of this patent is extended or adjusted under 35 U.S.C. 154(b) by 0 days.

(21) Appl. No.: 10/330,423

(22) Filed: Dec. 30, 2002

(65) Prior Publication Data

US 2003/0135119 A1 Jul. 17, 2003

(30) Foreign Application Priority Data

Dec. 31, 2001 (KR) ........................................ 2001-88872

(51) Int. Cl.[7] ............................................... A61B 8/14
(52) U.S. Cl. ...................................................... 600/461
(58) Field of Search ................................ 600/437–462, 600/464, 300; 378/98.12; 606/1

(56) References Cited

U.S. PATENT DOCUMENTS

| 5,398,690 A | * | 3/1995 | Batten et al. ............... 600/461 |
| 5,638,819 A | | 6/1997 | Manwaring et al. |
| 5,758,650 A | * | 6/1998 | Miller et al. ................ 600/461 |
| 5,930,329 A | * | 7/1999 | Navab ..................... 378/98.12 |
| 5,943,719 A | * | 8/1999 | Feldman et al. .................... 1/1 |
| 6,216,029 B1 | | 4/2001 | Paltieli |
| 6,241,670 B1 | | 6/2001 | Nambu |
| 6,423,009 B1 | * | 7/2002 | Downey et al. ............ 600/461 |

FOREIGN PATENT DOCUMENTS

| EP | 1 083 443 | 3/2001 |
| KR | 10-0308230 | 8/2001 |
| WO | WO 99/16352 | 4/1999 |

* cited by examiner

*Primary Examiner*—Dennis W. Ruhl
*Assistant Examiner*—Ruby Jain
(74) *Attorney, Agent, or Firm*—Oblon, Spivak, McClelland, Maier & Neustadt, P.C.

(57) ABSTRACT

A method and apparatus for enabling a biopsy needle to be observed in a three-dimensional ultrasound diagnostic system using an interventional ultrasound system. The apparatus comprises an ultrasound transducer, a three-dimensional image-forming section, a section for extracting a target object, a location-calculating section, a display section, and a controller. The method comprises the steps of acquiring a two-dimensional ultrasound image of a subject; generating a three-dimensional volume image based on the two-dimensional ultrasound image; segmenting a target image, which corresponds to a target object within the subject, from the three-dimensional volume image; displaying a guide line of the biopsy guide on the segmented target image; extracting the segmented target image; acquiring information on a location of the biopsy needle by reference to the segmented target image; calculating an error based on the information; and displaying a guiding status of the biopsy needle based on the calculated error.

9 Claims, 5 Drawing Sheets

METHOD AND APPARATUS FOR ENABLING A BIOPSY NEEDLE TO BE OBSERVED

FIELD OF THE INVENTION

The present invention relates to an ultrasound diagnostic system, and more particularly, to a method and apparatus for observing a biopsy needle and guiding the same towards a target object within the human body in a three-dimensional ultrasound diagnostic system that uses interventional ultrasound system.

BACKGROUND OF THE INVENTION

In the field of interventional ultrasound imaging, a medical procedure is performed which, for diagnostic or treatment purposes, takes a sample of a target object, for example, the tissue of a specific internal organ of the patient's body by inserting a medical device such as a biopsy needle into the patient's body and, at the same time, monitoring the movement of such medical device within the patient's body in real time with the use of the ultrasound diagnostic system. Thus, in order to ensure reliable diagnosis, it is necessary to display an ultrasound image in such manner that a positional relationship between the target object and the biopsy needle can precisely be identified.

However, since a conventional two-dimensional ultrasound diagnostic system displays the biopsy needle in a plane defined by the axial and lateral directions of the transducer, it is difficult to precisely identify the location of the biopsy needle in the displayed ultrasound image when a movement in elevation of the biopsy needle occurs. A similar problem arises for the two-dimensional ultrasound diagnostic system which can generate a two-dimensional B-mode image of human organs and can show the guide line of the biopsy needle on the image being displayed by using a geometrically adequate biopsy guide. More specifically, since the transducer used in the two-dimensional ultrasound diagnostic system has to perform beam-focusing in the direction of elevation as well, it is not viable to display the movement in elevation of the biopsy needle in a two-dimensional image when the biopsy needle is not located in a plane defined by the axial and lateral directions, i.e., when the movement of the biopsy needle is to the direction of elevation. The difficulty in observing a target object in the displayed ultrasound image is attributed mainly to the fact that most of the target objects take a form of a three-dimensional sphere, while the two-dimensional ultrasound diagnostic system displays only a sectional view of the portion where the transducer is currently located. Therefore, visualization capabilities of a target object to be subject to a tissue inspection are inevitably restricted by the inherent characteristics of the two-dimensional ultrasound diagnostic system.

In an attempt to circumvent the above problems, a three-dimensional ultrasound diagnostic system is often used when performing a medical inspection, where a biopsy needle is used, due to the fact that a positional relationship between the biopsy needle and the target object can clearly be observed in a volume image provided by the three-dimensional ultrasound diagnostic system. Among the several methods for observing the biopsy needle adopted for the three-dimensional ultrasound diagnostic system, the following two methods are known as being most widely used. The first is a method wherein the biopsy guide is attached to the transducer as in a conventional two-dimensional diagnostic system, and the biopsy needle is displayed by using known information on a geometrical structure of the biopsy needle; and the other is a method called "a free-hand style method." In the free-hand style method, the location of the biopsy needle is discerned by the user's estimation or sensation wherein the user holds a three-dimensional transducer with one hand as shown in FIG. 1, and manipulates the biopsy needle with the other hand without using the biopsy guide.

As described above, the three-dimensional ultrasound diagnostic system can also provide a guide line as is provided by a two-dimensional ultrasound diagnostic system, in case that the biopsy guide is used. However, in a display image showing a volume rendered with respect to x, y and z axes, the biopsy needle is typically displayed on one of the three planes defined by the x, y and z axes. Thus, unless the three-dimensional ultrasound image is rearranged, it is difficult to precisely observe the movement of the biopsy needle since the biopsy needle is indicated merely as a point in the rendered image. The free-hand style method cannot display a location of the biopsy needle precisely. Further, for the free-hand style method, diagnosis is performed mainly by estimation or sensation of the user so that the accuracy of diagnosis depends on the skill of the user.

SUMMARY OF THE INVENTION

It is accordingly an object of the present invention to provide a method and apparatus for accentuating a relationship between a biopsy needle and a target object by contouring the biopsy needle in a three-dimensional ultrasound image provided by a three-dimensional ultrasound diagnostic system.

It is another object of the present invention to provide a method and apparatus for automatically guiding a biopsy needle into the human body by automatically extracting a target object from a three-dimensional ultrasound image, contouring the target object, and obtaining information on locations of and a relationship between the extracted target object and the biopsy needle being guided.

In accordance with one aspect of the present invention, an apparatus for enabling a biopsy needle to be observed in a three-dimensional ultrasound image is provided which comprises means for transmitting ultrasound signals towards a target object and receiving echo signals reflected from the target object; means for forming a three-dimensional volume image by receiving and combining two-dimensional data from the transmitting means; means for extracting the target object from the three-dimensional volume image; means for estimating a location of the extracted target object and a location of the biopsy needle that is inserted into the extracted target object; means for displaying the extracted target object; and means for calculating an error in location between the biopsy needle and the extracted target object based on the estimation and providing the calculated error to the estimating means.

In accordance with another aspect of the present invention, a method of enabling a biopsy needle to be observed in a three-dimensional ultrasound image is provided which comprises the steps of acquiring a two-dimensional ultrasound image of a subject; generating a three-dimensional volume image based on the two-dimensional ultrasound image; segmenting a target image, which corresponds to a target object within the subject, from the three-dimensional volume image; displaying a guide line of the biopsy guide on the segmented target image; extracting the segmented target image; acquiring information on a location of the biopsy needle by reference to the segmented target image; calculating an error based on the information;

BRIEF DESCRIPTION OF THE DRAWINGS

The features, objects, and advantages of the present invention may best be understood with reference to the following description, taken in conjunction with the accompanying drawings.

DETAILED DESCRIPTION OF THE PRESENT INVENTION

Figure 1:
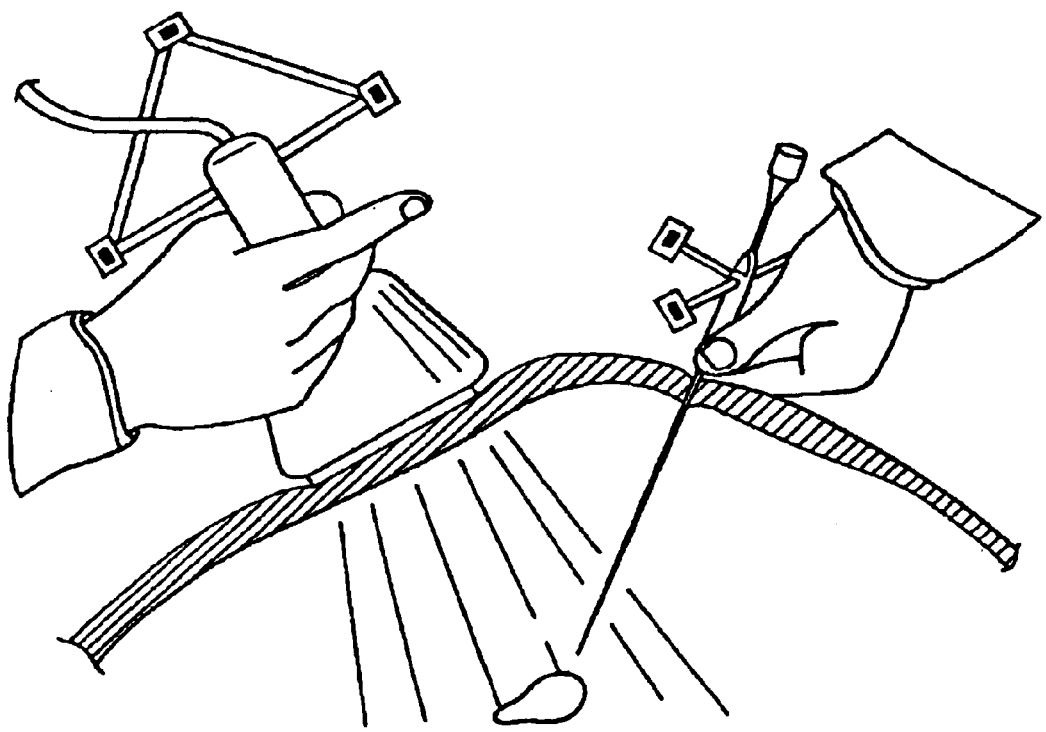
FIG. 1 shows a structure of a conventional interventional ultrasound imaging system.
Figure 2:
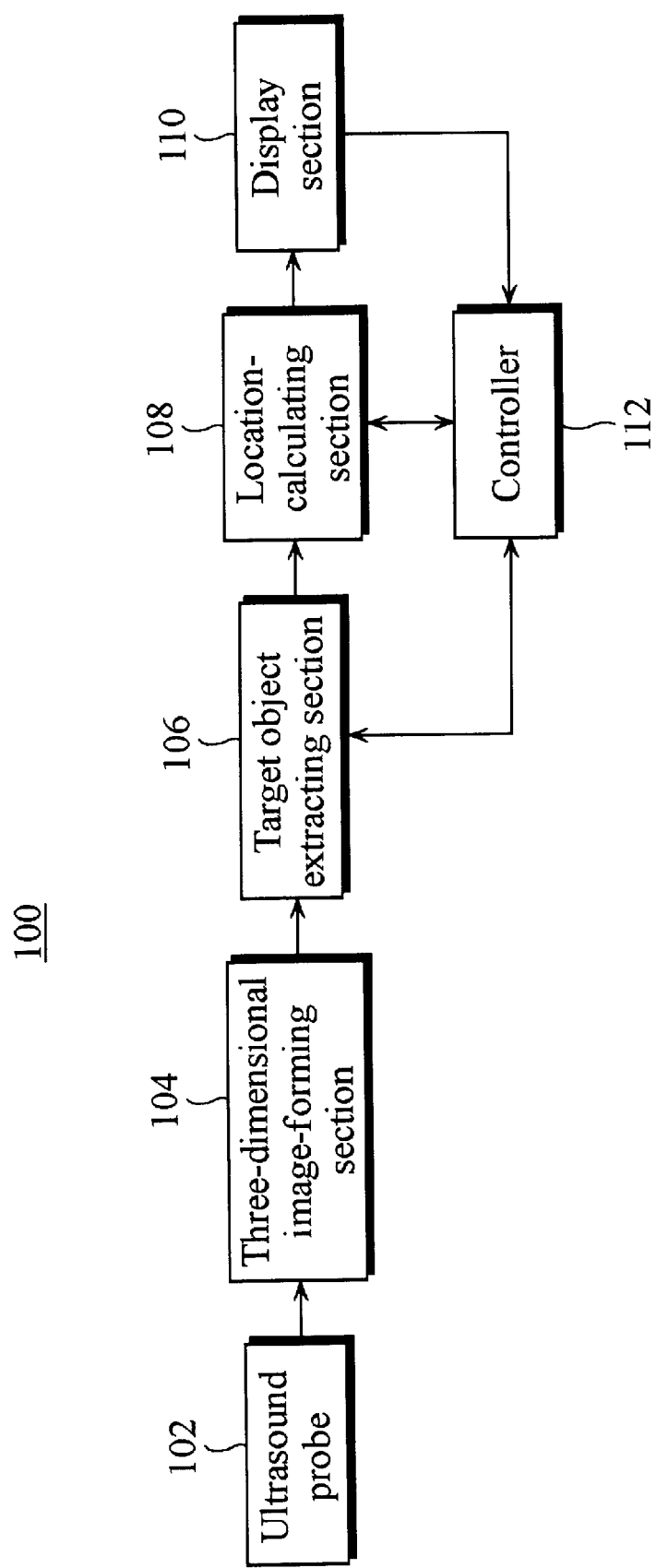
FIG. 2 shows a schematic block diagram of an apparatus for enabling observation of a biopsy needle in a three-dimensional ultrasound image according to the present invention.

Referring to FIG. 2, there is shown a schematic block diagram of an apparatus for enabling observation of a biopsy needle in a three-dimensional ultrasound image according to the present invention. As shown in FIG. 2, a guiding apparatus 100 comprises an ultrasound transducer 102, a three-dimensional image-forming section 104, a section for extracting a target object 106, and a location-calculating section 108, a display section 110, and a controller 112. Ultrasound transducer 102 serves to transmit ultrasound signals towards a target object and receive echo signals reflected from the target object. Either a rotated transducer by motor or an electronic transducer with piezo-electric elements arranged two dimensionally may be used as ultrasound transducer 120. However, input data format differs depending on which transducer is used for ultrasound transducer 102. To this end, a coordinate system defined by an angle and a distance or a three-dimensional rectangular coordinate system may be chosen to adequately represent the locations of pixels. Three-dimensional image-forming section 104 combines continuous two-dimensional data inputted from ultrasound transducer 102 to produce three-dimensional volume data.

Section for extracting a target object 106 extracts a target object from the three-dimensional volume data inputted from three-dimensional image-forming section 104. In this case, a boundary of the target object may be extracted by using the image processing technique called "Virtual Organ Computer Aided Analysis (VOCAL)" disclosed in Korean Patent No. 10-0308230, issued Aug. 27, 2001 and in European Patent Application No. EP 1 083 443 A2, entitled ULTRASONIC IMAGE APPARATUS FOR SEPARATING OBJECT, wherein each of internal organs of the human body to be diagnosed is separately extracted and visualized in a three-dimensional ultrasound image. In addition to the automatic extraction capabilities, the section for extracting a target object 106 can extract a target object drawn by the user. The extraction of a boundary of a drawn target object may be performed by either a three-dimensional segmentation based on the three-dimensional technique or by continuously segmenting the two-dimensional volume data and manipulating them three dimensionally.

Figure 3A:
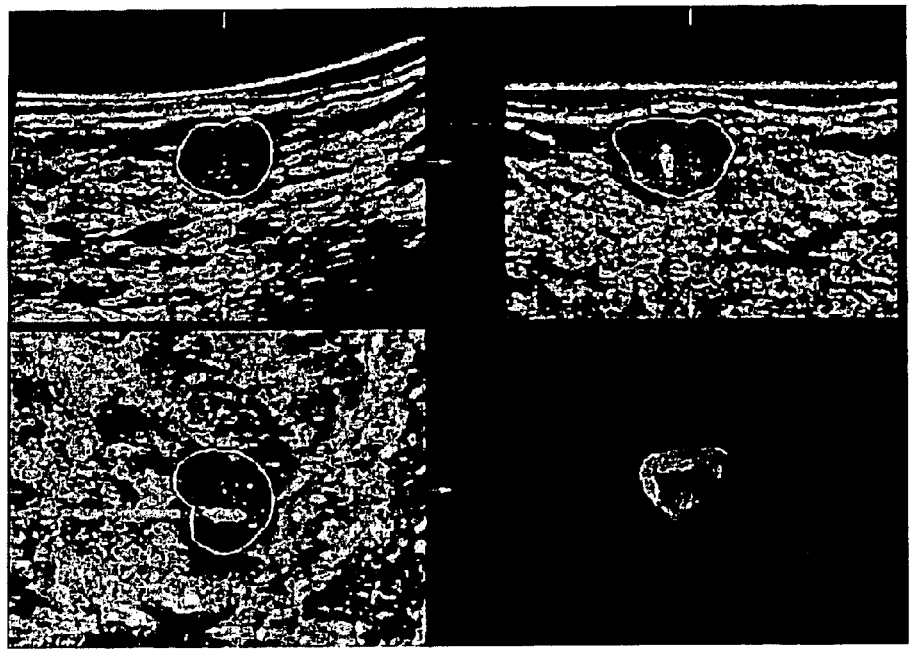
FIGS. 3a and 3b show ultrasound images to explain a procedure for extracting a target object from three-dimensional ultrasound image data acquired in accordance with the present invention.
Figure 3B:
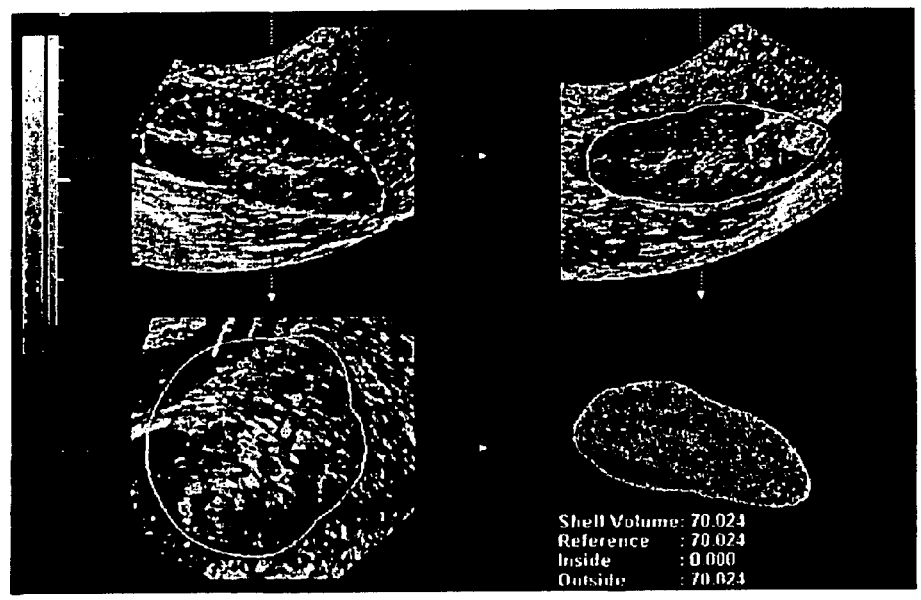

FIGS. 3a and 3b show ultrasound images to explain a procedure for extracting a target object from three-dimensional ultrasound image data acquired in accordance with the present invention. FIG. 3a illustrates an image resulting from three dimensionally rendering the boundary of the target object as drawn by the user in a xyz plane. The rendered image of the target object with its boundary contoured as shown in FIG. 3 can be advantageously used when an automatic extraction of the boundary of the target object is not feasible as in most of the ultrasound images or when the ultrasound imaging system being used is not equipped with such automatic extraction capabilities. FIG. 3b shows an image where the boundary of the target object has been extracted. After extracting a two-dimensional boundary of the target object in a xyz plane, a three dimensionally rendered image can be displayed.

As mentioned above, section for extracting a target object 106 in accordance with the present invention performs processing on continuous volume data, and thus can extract and display the target object by performing motion estimation instead of performing real-time continuous segmentation. Thus, section for extracting a target object 106 acquires motion information of the target object in motion and provides location information helpful in extracting the next target object. Assuming that there is a target object previously extracted by the first extracting step during the process of continuously extracting the target object, the entire or some sample blocks in the previously extracted target object are pattern-matched with the neighboring areas of the subsequently extracted target object. Through this process, the final location of the target object can be calculated, and the calculation indicates that the target object has moved by the calculated distance. Therefore, it is possible to finely and automatically modify the contour extracted from the previous volume based on the location information.

Location-calculating section 108 calculates a center of gravity of the target object based on a geometric shape of the extracted target object, and obtains information on the location of the biopsy needle as represented as a three-dimensional shape in the spatial coordinate system. The reason why the center of gravity of the target object is calculated is that the biopsy needle must be inserted into the center area of the target object, and calculating a center of gravity is known as the most widely used method for finding a center of a geometric object. Based on the calculated center of gravity of the target object, location-calculating section 108 can thus estimate a motion of the target object currently in motion, and allows guiding apparatus 100 to estimate the direction of advance of the biopsy needle.

Display section 110 displays the extracted target object based on the well-known computer graphics techniques. Display section 110 may display only the extracted target object in isolation, and may alternatively display only the boundary of the target object against the background.

Controller 112 controls display section 110 to display a motion of the target object, the path of the biopsy needle currently being guided as calculated, and the ideal path between the target object and the biopsy needle whose information is useful for accurately guiding the biopsy needle. Controller 112 further controls display section 110 to display numerical information on an error between the ideal path and the actual path of the biopsy needle, together with graphics. Provided guide lines have a cylindrical shape with a fixed diameter. When the biopsy guide line is provided, the error is indicative of how the biopsy needle is parallel with the biopsy guide line or how closely the biopsy needle moves along the center of the biopsy guide line. With the numerical information on the error, an angle between the biopsy needle and the biopsy guide line, and a distance between the center of the biopsy guide line and the tip of the biopsy needle can be defined as useful parameters.

Figure 4A:
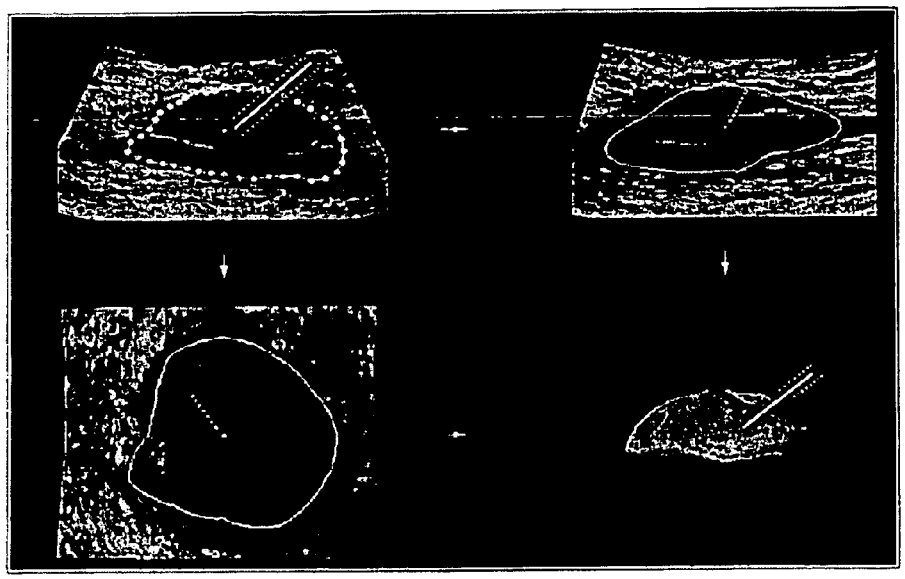
FIGS. 4a and 4b show ultrasound images to explain a procedure for guiding a biopsy needle by extracting a target object in accordance with the present invention.
Figure 4B:
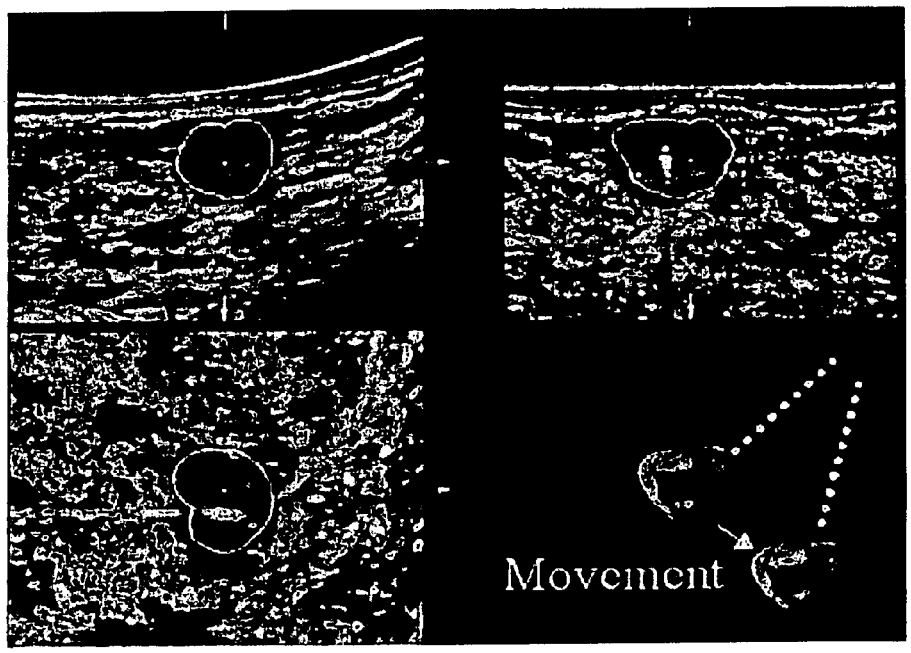

Referring now to FIGS. 4a and 4b, ultrasound images are shown which explain a procedure for guiding a biopsy needle by extracting a target object in accordance with the present invention. In particular, FIG. 4a illustrates the boundary of the target object extracted on the xyz plane, and indicates how the biopsy needle is located in the three-dimensional image rendered with the use of information on the boundary. FIG. 4b illustrates a process where the target object or the biopsy needle is tracked by exploiting the automatic tracking capabilities.

Controller 112 further controls guiding apparatus 100 by using information on the center of gravity of the extracted target object, which is calculated in location-calculating section 108, and information on the location of the biopsy needle. First, controller 112 determines whether the direction to which the biopsy needle is currently guided is correct by using information on the center of gravity and information on the location of the biopsy needle and, if an error is found, provides error information to location-calculating section 108 so that it can calculate and compensate the error. In this case, the error represents an error in terms of the biopsy needle's movement that is predicted to be generated as the biopsy needle is guided. The error is calculated based on information on the location of the extracted target object and information on the relative location of the biopsy needle. Next, controller 112 provides to section for extracting a target object 106 location-related information that is helpful in sensing a motion of the target object and segmenting/extracting the next target object.

Figure 5:
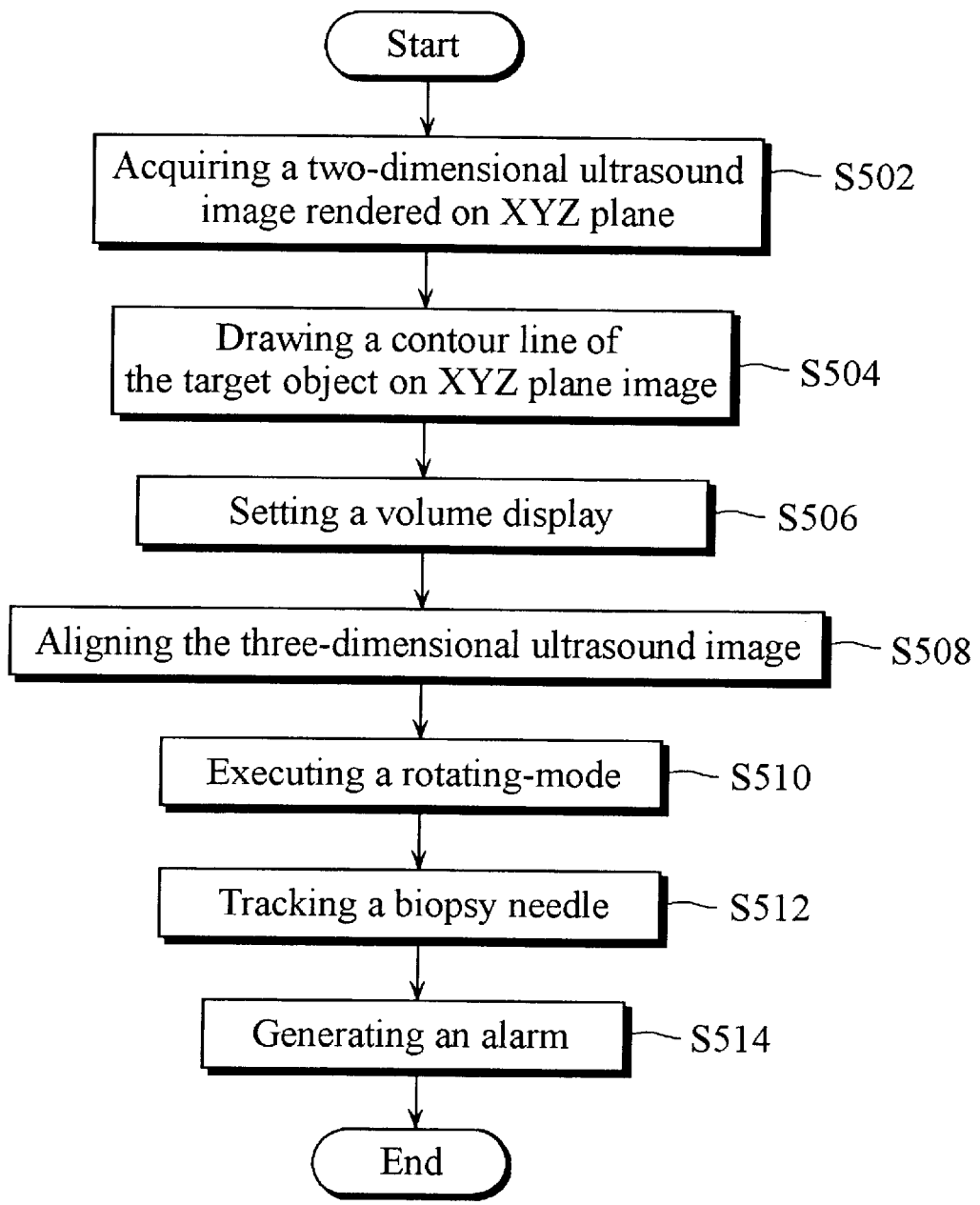
FIG. 5 shows a flowchart to explain a procedure for observing a biopsy needle in a three-dimensional ultrasound image provided in accordance with the present invention.

Next, a procedure for observing a biopsy needle in a three-dimensional ultrasound image provided in accordance with the present invention will be explained with reference to the flowchart shown in FIG. 5. The procedure starts at step S502 where two-dimensional ultrasound images are consequently acquired through ultrasound transducer 102 and a volume image is generated by three-dimensional image-forming section 104 based on the acquired two-dimensional ultrasound image. In this case, once the biopsy guide line is set within the volume, the volume is rotated to be displayed as a straight line on the xy plane so that the biopsy guide line is displayed as a solid line on the xy palne.

At step S504, the desired target object is rendered along the contour line which the user drew on the xyz plane image as acquired by section for extracting a target object 106, or otherwise the target object as automatically segmented based on the VOCAL technique is designated. At step S506, the center of the extracted target object is found by location-calculating section 108, and the volume display is set so that the target object is placed at the center of the volume display. Then, a figure indicative of the target object is displayed at the center of the xy plane image, as shown in FIGS. 3a and 3b, and the biopsy guide line is displayed to extend up to the center of the target object (i.e., the center of the plane). On the z plane, on the other hand, the biopsy guide line is displayed as a point on the center of the figure of the target object.

At step S508, the xyz plane image and rendered volume display are aligned. For the free-hand style method, since information on the geometric structure of the biopsy needle is not available, it is not possible to display the predicted biopsy guide line. In this case, the VOCAL technique is applied to segment the biopsy needle, and the location of the biopsy needle is found within the volume. Based on the location of the biopsy needle as found, displays relating to the biopsy needle are aligned on the xyz plane and rendered volume display.

At step S510, in order to display the guiding status of the biopsy needle, the rendered volume image as displayed together with the xyz plane image is rotated by a predetermined angle to the counter-clockwise direction and in turn to the clockwise direction. The reason for rotating the rendered volume image is that an image rendered from extracting the two or three-dimensional boundary or an image obtained based on the volume rendering method is displayed on the two-dimensional display screen, and therefore, the viewer may not feel the cubic effect if he continues to see such image. In this display mode, since the rendered image, which otherwise may become a 2.5 dimensional image, is displayed more like a three-dimensional image, the operator can observe the biopsy needle moving in the space.

At step S512, the biopsy needle is continuously tracked by using the live VOCAL technique. At the same time, the target object is also tracked so that a relationship between the biopsy needle and the target object can be clearly recognized on the xyz plane and volume image. More specifically, an image like that obtained when an endoscope camera is attached to the biopsy needle is added to the xyx plane image. Then, the user can visually appreciate the motion of the biopsy needle that approaches toward the target object. The target object is seen perspectively in the rendered status as if it is zoomed-in. As a result, the tissue that is found by the VOCAL technique based on the location of the tip of the biopsy needle can be seen as if an onion shell is peeled.

At step S514, an alarm is generated as the biopsy needle approaches the target object. Once the biopsy needle approaches within a predetermined distance from the target object, an alarm having a long intermittence period and low frequency is first generated. As the biopsy needle further approaches the target object, an alarm having a relatively short intermittence period and high frequency is generated to alert that the biopsy needle is approaching near the target object. When the tip of the biopsy needle reaches the center of the target object, a continuous alarm is generated. Similarly, the color for the background of the z plane in the xyz plane image progressively turns into a brighter color, when the biopsy needle approaches the target object. This can give a visual alarm effect.

For either case when the free-hand style method or the method using the biopsy guide is used, the biopsy needle cannot be aligned on any of the x-y-z planes under certain situations. In this case, the biopsy needle is first found from the volume, and then geometric information on the biopsy needle is extracted. Thereafter, the aligned xyz plane image and volume image are formed, in the manner as mentioned above.

If the biopsy needle is used in an image mode other than the aligned xyz plane image mode or the volume image mode, the biopsy guide line having perspective is graphically displayed with respect to a point where the biopsy needle is currently passing. If the biopsy needle is tracked, such biopsy guide line is continuously displayed in the xyz plane, and the operator may change the angle of view as the biopsy needle is guided.

In accordance with the present invention, the biopsy needle can be aligned and displayed on the xyz plane. Also, a motion of the biopsy needle or the target object can be tracked so that a relationship between the biopsy needle and the target object can be clearly observed. Therefore, it is possible to enable the biopsy needle to exactly reach the target object. The prior art problem that the accuracy of diagnosis may depend on the skill of the user can also be eliminated.

While particular embodiments of the present invention have been shown and described, it will be obvious to those skilled in the art that changes and modifications may be made without departing from this invention in its broader aspects and, therefore, the aim in the appended claims is to cover all such changes and modifications, as fall within the true spirit and scope of this invention.

What is claimed is:

1. An apparatus for enabling a biopsy needle to be observed in a three-dimensional ultrasound image comprising:

means for transmitting ultrasound signals towards a target object and receiving echo signals reflected from the target object;

means for forming a three-dimensional volume image by receiving and combining two-dimensional data from said transmitting means;

means for extracting the target object from the three-dimensional volume image;

means for estimating a location of the extracted target object and a location of the biopsy needle that is inserted into the extracted target object;

means for displaying the extracted target object;

means for calculating an error in location between the biopsy needle and the extracted target object based on said estimation and providing the calculation error to said estimating means, wherein said means for extracting extracts the target object based on one of a continuous segmentation and extraction process, and a motion estimation process; and wherein said means for estimating finds a center of gravity of the extracted target object to estimate the location of the extracted target object.

2. The apparatus according to claim 1, wherein said means for displaying displays a path between the extracted target object and the biopsy needle that is to be followed by the biopsy needle.

3. The apparatus according to claim 1, wherein the error is an error in terms of location of the biopsy needle to be generated as the biopsy needle is guided toward the extracted target object.

4. A method of enabling a biopsy needle to be observed in a three-dimensional ultrasound image, comprising the steps of:

acquiring a two-dimensional ultrasound image of a subject;

generating a three-dimensional volume image based on the two-dimensional ultrasound image;

segmenting a target image, which corresponds to a target object within the subject, from the three-dimensional volume image;

displaying a guide line of the biopsy needle on the segmented target image;

extracting the segmented target image;

acquiring information on a location of the biopsy needle by reference to the segmented target image;

calculating an error based on the information; and displaying a guiding status of the biopsy needle based on the calculated error, wherein said extracting step includes calculating a center of gravity of the segment target image.

5. The method according to claim 4, wherein the two-dimensional ultrasound image includes images on x, y and z planes of a rectangular coordinate system.

6. The method according to claim 5, wherein the two-dimensional ultrasound image is aligned with respect to the biopsy needle to form the three-dimensional volume image.

7. The method according to claim 6, wherein the three-dimensional volume image is generated through a rendering process and based on the two-dimensional ultrasound image.

8. The method according to claim 4, wherein the error is an error in terms of location of the biopsy needle within the segmented target image that is to be generated as the biopsy needle is guided toward the target object, said error being calculated with reference to the information on a location of the biopsy needle and information on a location of the target object.

9. An apparatus for enabling a biopsy needle to be observed in a three-dimensional ultrasound image comprising:

means for transmitting ultrasound signals towards a target object and receiving echo signals reflected from the target object;

means for forming a three-dimensional volume image by receiving and combining two-dimensional data from said transmitting means;

means for extracting the target object from the three-dimensional volume image;

means for estimating a location of the extracted target object and a location of the biopsy needle that is inserted into the extracted target object;

means for displaying the extracted target object; and means for calculating an error in location between the biopsy needle and the extracted target object based on said estimation and providing the calculation error to said estimating means, wherein said means for estimating finds a center of gravity of the extracted target object to estimate the location of the extracted target object.

* * * * *